United States Patent [19]

Lang et al.

[11] Patent Number: 4,710,584
[45] Date of Patent: Dec. 1, 1987

[54] DERIVATIVES OF 3-BENZYLIDENE CAMPHOR, PROCESS FOR THEIR PREPARATION AND THEIR USE AS PROTECTIVE AGENTS AGAINST UV RAYS AND AS MEDICAMENTS

[75] Inventors: Gerard Lang, Saint Gratien; Serge Forestier, Claye Souilly; Alain LaGrange, Chatou, all of France

[73] Assignee: L'Oreal, Paris, France

[21] Appl. No.: 680,559

[22] Filed: Dec. 11, 1984

[30] Foreign Application Priority Data

Dec. 14, 1983 [LU] Luxembourg ............................ 85139

[51] Int. Cl.$^4$ .................... C07L 69/76; C07L 143/52
[52] U.S. Cl. ........................ 560/51; 562/462;
564/169; 568/326; 568/327; 260/507 R;
514/545; 514/510; 514/517; 560/19
[58] Field of Search ................... 560/51, 19; 562/462;
564/169; 568/326, 327; 514/545

[56] References Cited

U.S. PATENT DOCUMENTS

| | | | |
|---|---|---|---|
| 3,781,417 | 12/1973 | Welters et al. | 560/19 |
| 4,061,730 | 2/1976 | Kalopissis et al. | 560/19 |
| 4,165,336 | 8/1979 | Bouillon et al. | 560/19 |
| 4,250,108 | 2/1981 | Bouillon et al. | 560/19 |
| 4,304,730 | 12/1981 | Bouillon et al. | 560/19 |
| 4,323,549 | 1/1976 | Bouillon et al. | 560/19 |
| 4,327,031 | 4/1982 | Bouillon et al. | 560/19 |
| 4,330,488 | 5/1982 | Bouillon et al. | 560/19 |
| 4,421,739 | 12/1983 | Bouillon et al. | 560/19 |
| 4,585,597 | 4/1986 | Lang | 260/507 R |

FOREIGN PATENT DOCUMENTS

| | | |
|---|---|---|
| 2199971 | 4/1974 | France . |
| 2236515 | 2/1975 | France . |
| 2282426 | 3/1976 | France . |
| 2383904 | 10/1978 | France . |
| 2406647 | 5/1979 | France . |
| 2421878 | 11/1979 | France . |
| 2121801 | 1/1984 | United Kingdom . |

Primary Examiner—Paul J. Killos
Attorney, Agent, or Firm—Fleit, Jacobson, Cohn & Price

[57] ABSTRACT

New derivatives of 3-benzylidene camphor, process for preparing them and their use as protective agents against UV rays and as medicaments.

Derivatives of 3-benzylidene camphor of formula:

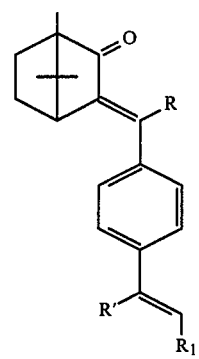

in which
R denotes a hydrogen atom, a methyl or ethyl radical,
R' denotes a hydrogen atom, a methyl or ethyl radical,
R and R' being unable simultaneously to denote a hydrogen atom,
$R_1$ denotes a $-COOR_2$, $-CONHR_2$, $-COO^-M^+$, $-CHO$, $-CH(OR_4)_2$ or $-CH_2OR_4$ group,
$R_2$ being an alkyl, alkenyl, cycloalkyl or aralkyl radical containing at most 20 carbon atoms, optionally substituted by hydroxy, alkoxy, amine or quaternary ammonium groups,
M denoting a hydrogen atom, an alkali metal or a $N^+(R_3)_4$ group, $R_3$ being a hydrogen atom or a $C_1$ to $C_4$ alkyl or hydroxyalkyl radical,
$R_4$ denoting H, alkyl, cycloalkyl or aralkyl containing at most 20 carbon atoms.

Application in cosmetics for protection against UV rays.

Therapeutic application for the treatment of dermatological and rheumatic complaints; anti-tumour activity.

27 Claims, No Drawings

DERIVATIVES OF 3-BENZYLIDENE CAMPHOR, PROCESS FOR THEIR PREPARATION AND THEIR USE AS PROTECTIVE AGENTS AGAINST UV RAYS AND AS MEDICAMENTS

The present invention relates to new compounds derived from 3-benzylidene camphor, as well as to a process for preparing them and to their use for protection against ultraviolet radiation in the cosmetic field and as medicaments.

It is known that light radiations of wavelengths of between 280 and 400 nm permit the suntanning of human skin and that rays of wavelengths of between 280 and 320 nm, known under the name UV-B also produce erythemas and skin burns which can be harmful to the development of the suntan.

The use of compounds active in the abovementioned wavelength range 280–320 nm is already known. U.S. Pat. No. 3,781,417 describes as a UV-B absorber 3-(4'-methylbenzylidene)-camphor the maximum absorption of which is situated at 297 nm. This compound has good solubility in oils, but is insoluble in water.

Other derivatives of benzylidene camphor are also known as having absorption properties in the wavelength range 280–320 nm. These are benzylidene camphor derivatives containing a quaternary ammonium radical on the benzene ring in the para position relative to the bornylidene radical according to French Patent No. 2,199,971, benzylidene camphor derivatives sulphonated on the methyl radical in position 10 of the camphor or in position 3' or 4' on the benzene ring according to French Patent Nos. 2,282,426 and 2,236,515, and derivatives of p-methylbenzylidene camphor substituted on the p-methyl group according to French Patent Nos. 2,383,904, 2,402,647 and 2,421,878.

It is also known that the components incorporated in cosmetic preparations, and in particular some colorants of dyeing compositions, coloured hair lacquers, shampoos, hair setting lotions, make-up products such as tinted creams, nail varnishes and lipsticks do not always have adequate light-stability and that they deteriorate under the effect of light radiations.

It has appeared desirable to widen the group of compounds capable of absorbing the UV-B rays, having good solubility in the usual cosmetic solvents and supports and protecting both human skin and the various products sensitive to these radiations by application on the skin or incorporation in the products, preparations and compositions which are sensitive to these radiations.

We have discovered that some derivatives of 3-benzylidene camphor had, suprisingly, good filtering properties in respect of the UV-B rays, were perfectly soluble in the usual cosmetic solvents and had good thermal stability and excellent photochemical stability.

A subject of the present invention is therefore new derivatives of 3-benzylidene camphor having the formula:

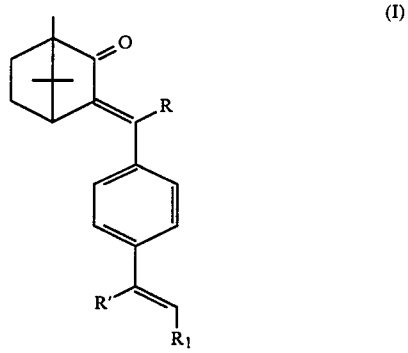

in which
R denotes a hydrogen atom, a methyl or ethyl radical,
R' denotes a hydrogen atom, a methyl or ethyl radical,
R and R' being unable simultaneously to denote a hydrogen atom,
$R_1$ denotes a —$COOR_2$, —$CONHR_2$, —$COO^-M^+$, —CHO, —$CH(OR_4)_2$ or —$CH_2OR_4$ group,
$R_2$ being an alkyl, alkenyl, cycloalkyl or aralkyl radical containing at most 20 carbon atoms, optionally substituted by hydroxy, alkoxy, amine or quaternary ammonium groups,
M denoting a hydrogen atom, an alkali metal or a $N^+(R_3)_4$ group, $R_3$ being a hydrogen atom or a $C_1$ to $C_4$ alkyl or hydroxyalkyl radical,
$R_4$ denoting a hydrogen atom or an alkyl, cycloalkyl or aralkyl radical containing at most 20 carbon atoms.

The preferred compounds are those in which R and R' do not simultaneously denote a methyl or ethyl radical.

Among the preferred radicals $R_2$ and $R_4$ mention may be made of the radicals: methyl, ethyl, propyl, butyl, hexyl and 2-ethylhexyl.

Depending on the nature of the substituent $R_1$, the compounds of the formula (I) according to the invention are hydrosoluble or liposoluble. When $R_1$ denotes a —$COOR_2$ or —$CONHR_2$ group, they are soluble in oils; when $R_1$ denotes —$COO^-M^+$, M being other than a hydrogen atom, they are soluble in water.

A process for preparing the new compounds of formula (I) is also a subject of the present invention.

The compounds of formula (I) are obtained according to the following three reaction schemes:

(1) R=H and R'=methyl or ethyl

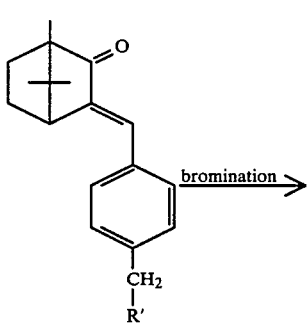

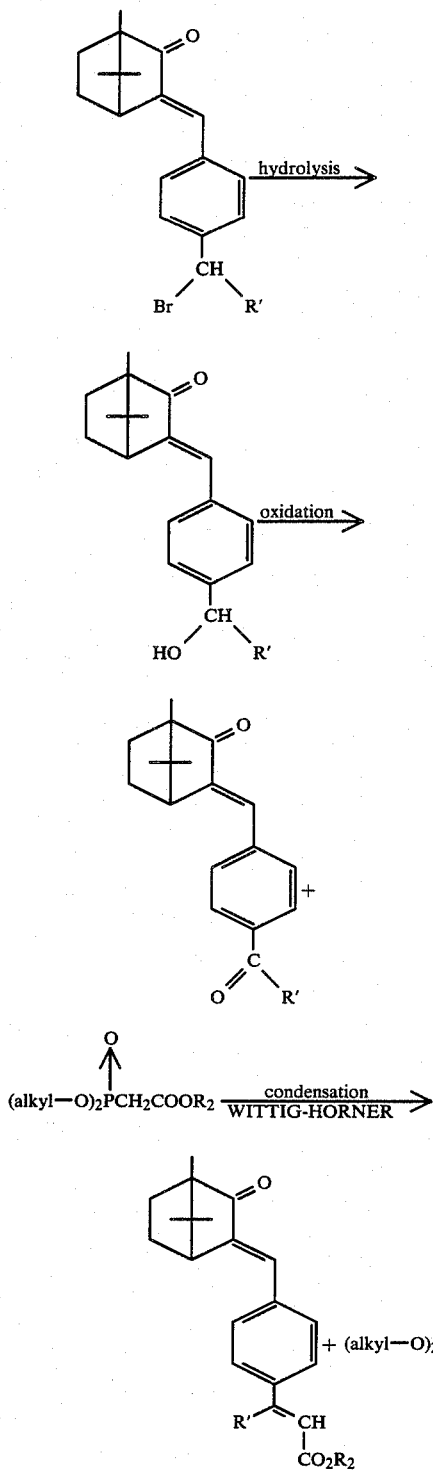

of a mixture of potassium dichromate and concentrated sulphuric acid. The last stage is a reaction known under the name of a Wittig condensation which can be defined as being the condensation of a triarylphosphonium salt with a carbonyl function to produce an unsaturated group or compound. This condensation is carried out in a polar solvent such as tetrahydrofuran in the presence of a strong base such as sodium hydride; in general, in the case where the cation combined with the base is sodium, very small quantities of 1,4,7,10,13-pentaoxacyclopentadecane are also added, the function of which is to increase the basicity of the medium. In the process of the invention, a phosphonate

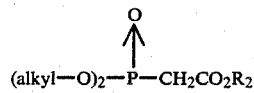

is employed instead of a phosphonium salt, the alkyl preferably denoting methyl or ethyl; consequently, it is a modified Wittig condensation which is involved (Wittig-Horner reaction).

(2) R=methyl or ethyl and R'=H

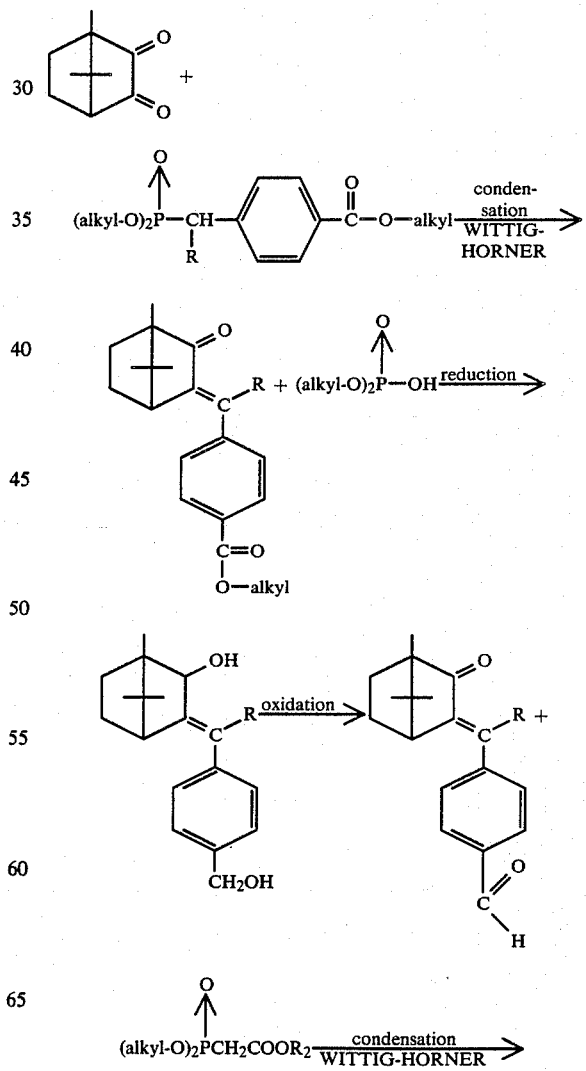

This process is a sequence of 4 conventional syntheses, the first being a bromination, usually carried out in an inert solvent medium with the aid of a brominating agent such as N-bromosuccinimide, at the reflux temperature of the mixture. This bromination is followed by a hydrolysis with sodium hydroxide, at a temperature in the region of 100° C., of the bromo derivative obtained. The third stage consists of an oxidation of a secondary alcohol to ketone with the aid, for example -continued

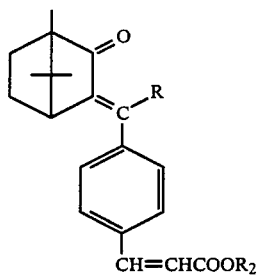

The first and the fourth stages are Wittig-Horner condensations employing a phosphonate in which of the alkyl preferably denotes methyl or ethyl, which are carried out under the operating conditions defined above in (1).

The second and third stages employing conventional procedures, which are the reduction of an alkoxycarbonyl group with the aid of a powerful reducing agent such as lithium aluminium hydride in an inert solvent medium to obtain the primary alcohol, and the oxidation of this alcohol function to an aldehyde function, for example by the action of pyridinium chlorochromate.

(3) R and R' simultaneously denote methyl or ethyl

The 1-(2'-oxo-3'-bornylidene)-1-(4'-formylphenyl)ethane or the 1-(2'-oxo-3-bornylidene)-1-(4'-formylphenyl)propane obtained in the third stage of the reaction scheme (2) above may be reacted with an organomagnesium compound such as methylmagnesium or ethylmagnesium bromide or iodide to convert the aldehyde to secondary alcohol, which is subjected to oxidation to obtain the ketone, which is finally condensed with a phosphonate in accordance with the Wittig-Horner reaction to obtain the required compounds.

In the above three reaction schemes, the compounds (I) in which $R_1$ denotes —$COOR_2$ are obtained. Using saponification, these compounds are converted into corresponding acids in which $R_1$ denotes —COOH, which may be converted to salts with an alkaline base or an amine to yield the compounds (I) where $R_1$ denotes $COO^-M^+$, $M^+$ being an alkali metal ion or a $N^+(R_3)_4$ group.

Using a known process, it is also possible to convert the acid to acid chloride by reaction with phosphorus trichloride, the acid chloride then being reacted with an amine to form the corresponding amide of formula (I) in which $R_1$ denotes —$CONHR_2$.

The esters of formula (I) in which $R_1$ denotes —$COOR_2$ may be reduced to form the alcohols, that is to say the compounds of formula (I) in which $R_1$ denotes —$CH_2OH$. The corresponding aldehydes are obtained by oxidation of the alcohols.

The acetals of formula (I) in which $R_1$ denotes —CH($OR_4$)$_2$ are derived from the aldehydes by the addition of alkanols, cycloalkanols or aralkyl alcohols to the latter in an acid medium. They can also be obtained by the addition of aldehydes to the compound of formula (I) in which $R_1$ denotes —$CH_2OH$, in an acid medium.

The ethers of formula (I) in which $R_1$ denotes —$CH_2OR_4$ are obtained from the corresponding alcohols by reaction with an alkyl, cycloalkyl or aralkyl halide.

The compounds according to the invention of formula (I) are illustrated by the following non-restrictive examples:

EXAMPLE 1

Preparation of a compound of general formula (I) in which:

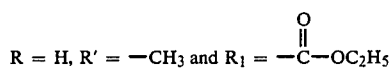

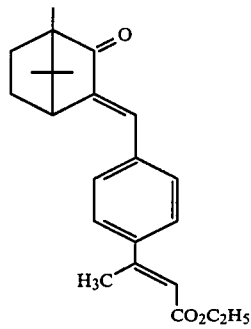

(1) Preparation of 4'-bromoethyl-3-benzylidene-camphor of formula:

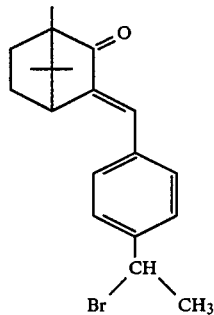

A solution of 34.8 g of 4'-ethyl-3-benzylidene-camphor, 25 g of N-bromosuccinimide and 0.300 g of azobisisobutyronitrile in 500 cm³ of $CCl_4$ is heated for one hour under reflux. It is allowed to return to ambient temperature and the succinimide is filtered off. The organic phase is washed with sodium bicarbonate, then with water and the solvent is evaporated off. 37 g of 4'-bromoethyl-3-benzylidene-camphor are obtained.

(2) Preparation of 4'-hydroxyethyl-3-benzylidene-camphor of formula:

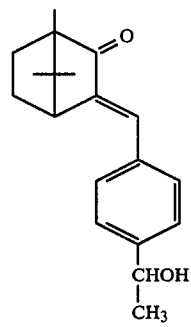

A suspension of 30 g of 4'-bromoethyl-3-benzylidene-camphor obtained above in 200 cm³ of 3N sodium hydroxide is heated for 6 hours at 100° C. At the end of reaction, the product is extracted with ether. The organic phase is washed with water and then dried over sodium sulphate. After evaporation, 21 g of 4'-hydroxyethyl-3-benzylidene-camphor are obtained.

(3) Preparation of 4'-acetyl-3-benzylidene-camphor of formula:

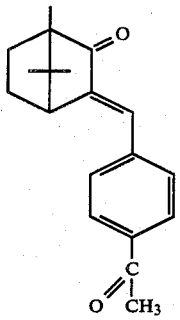

14 g of potassium dichromate are dissolved in 12 g of concentrated sulphuric acid and 75 g of ice. 20 g of 4'-hydroxyethyl-3-benzylidene-camphor are added.

The mixture is heated for 15 minutes at 80° C. and allowed to cool. It is extracted with ether, the organic phase is washed with water, dried over sodium sulphate and the solvent is evaporated off under reduced pressure. The product is purified by chromatography on silica gel (elution with dichloromethane). 8.2 g of 4'-acetyl-3-benzylidene-camphor are obtained.

(4) Condensation of 4'-acetyl-3-benzylidene-camphor with triethyl phosphonoacetate.

0.35 g of sodium hydride at a concentration of 50% in oil and 0.30 g of 1,4,7,10,13-pentaoxacyclopentadecane are added to a solution of 1.58 g of triethyl phosphonoacetate in 20 cm$^3$ of anhydrous THF. A solution of 2 g of 4'-acetyl-3-benzylidene-camphor in 10 cm$^3$ of anhydrous THF is added dropwise. The reactants are stirred for 1 hour at ambient temperature. The reaction medium is poured into cold water. It is extracted with ether, the organic phase is washed with a saturated solution of sodium bicarbonate and then with water. The solvent is evaporated off and the product is purified by chromatography on silica gel (eluent: 95:5 toluene-ethyl acetate). 1.3 g of a viscous, pale yellow liquid having the following characteristics are obtained:

Elemental analysis:

|  | C | H | O |
|---|---|---|---|
| Calculated | 78.41 | 7.95 | 13.64 |
| Found | 78.36 | 7.97 | 13.67 |

$\lambda$max=315 nm; $\epsilon$=35,800 (methanol).

EXAMPLE 2

Preparation of a compound of general formula (I) in which:

R = H, R' = —CH$_3$ and R$_1$ = —CO$_2$H

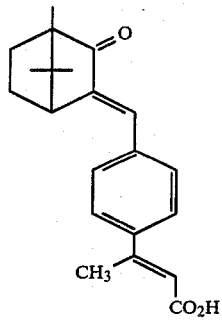

1 g of the compound obtained in Example 1 is dissolved in 25 cm$^3$ of ethanol. 5 cm$^3$ of 3N sodium hydroxide are added and heated under reflux for 1 hour. 25 cm$^3$ of water are added and the alcohol is distilled off. The mixture is acidified with 3N HCl and filtered. It is washed and dried under vacuum. 0.8 g of acid having the following characteristics is obtained:

Elemental analysis:

|  | C | H | O |
|---|---|---|---|
| Calculated | 77.78 | 7.41 | 14.81 |
| Found | 77.72 | 7.37 | 14.91 |

$\lambda$max=318 nm; $\epsilon$=30,000 (ethanol).

EXAMPLE 3

Preparation of a compound of general formula (I) in which:

$$R = H, R' = -CH_3 \text{ and } R_1 = -\overset{O}{\overset{\|}{C}}-NH-C_2H_5$$

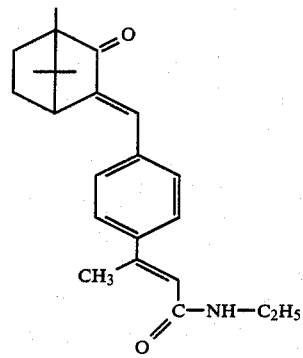

2 g of the acid obtained in Example 2 are added to 30 cm$^3$ of benzene and 1 g of phosphorus trichloride. The reactants are heated at 50° C. under nitrogen until the product has dissolved. After 1 hour's heating the solvent is evaporated off under reduced pressure. The residue is redissolved in 20 cm$^3$ of ether and added dropwise at −30° C. to a solution of 1 g of ethylamine in 10 cm$^3$ of ether. The reaction mixture is returned to ambient temperature. It is stirred for 2 hours and then the organic phase is washed with water, dried over sodium sulphate and the solvent is evaporated off under reduced pressure. 1.5 g of product having the following characteristics is obtained:

Elemental analysis:

|  | C | H | N | O |
|---|---|---|---|---|
| Calculated: | 78.63 | 8.26 | 3.99 | 9.12 |
| Found: | 78.60 | 8.30 | 3.96 | 9.14 |

λmax=318 nm; ε=36,000 (ethanol).

EXAMPLE 4

Preparation of a compound of general formula (I) in which:

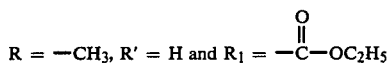
R = —CH₃, R' = H and R₁ = —C(=O)—OC₂H₅

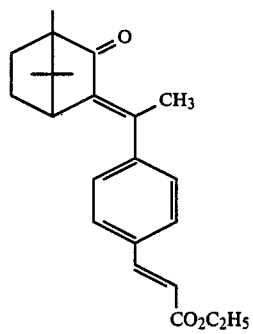

1.66 g of camphorquinone and 3 g of diethyl 4-methoxycarbonylphenylethylphosphonate are added to a suspension of 0.5 g of sodium hydride in 20 cm³ of tetrahydrofuran containing 0.05 g of 1,4,7,10,13-pentaoxacyclopentadecane. The reactants are stirred at ambient temperature overnight. The reaction medium is poured into water and the product is extracted with ethyl acetate. After the solvent has been distilled off the product is purified by chromatography on silica gel (solvent: hexane+5% ethyl acetate).

The compound obtained is dissolved in 50 cm³ of ether. 1 g of lithium aluminium hydride is added and the reactants are stirred overnight at ambient temperature. The excess hydride is destroyed with ethyl acetate. The mixture is diluted with water, extracted with ether and the organic phase is dried. After the solvent has been distilled off, 0.9 g of product is obtained and is redissolved in 50 cm³ of anhydrous dichloromethane. 1.9 g of pyridinium chlorochromate are added and the reaction mixture is stirred for 3 hours at ambient temperature. It is diluted with 50 cm³ of ether, filtered on Celite and the solvent is evaporated off. After purification on silica gel (solvent: hexane+2% of ethyl acetate), the product is added to a solution of 0.4 g of triethylphosphonoacetate in 1 cm³ of tetrahydrofuran containing 0.1 g of sodium hydride and 0.01 g of 1,4,7,10,13-pentaoxacyclopentadecane. The mixture is stirred for 1 hour at ambient temperature and then diluted with ether. The solution is filtered on Celite and the product is purified by chromatography on silica gel (solvent: hexane+2% of ethyl acetate). 0.5 g of product having the following characteristics is obtained:

Elemental analysis:

|  | C | H | O |
|---|---|---|---|
| Calculated | 78.41 | 7.95 | 13.64 |
| Found | 78.45 | 7.99 | 13.55 |

λmax=306 nm; ε=25,000 (chloroform).

Another subject of the present invention is a cosmetic composition containing, as a protective agent against the UV-B rays, at least one derivative of 3-benzylidene camphor of formula (I) according to the invention in a cosmetically acceptable medium.

The cosmetic composition according to the invention, when employed as a composition intended to protect human skin against ultraviolet rays, may be presented in the most diverse forms usually employed for this type of composition. It is presented particularly in the form of solution, lotion, emulsion such as a cream or a milk, aqueous-alcoholic or alcoholic gel, solid stick, or it may be packaged as an aerosol.

It may contain cosmetic adjuvants usually employed in this type of composition, such as thickeners, softeners, humectants, superfatting agents, emollients, wetting agents, surfactants, preserving agents, anti-foams, perfumes, oils, waxes, colorants and/or pigments the function of which is to colour the composition itself or the skin, bactericidal agents or any other ingredient usually employed in cosmetics.

The compound of formula (I) is present especially in proportions by weight of between 0.5 and 15% relative to the total weight of the composition.

A monoalcohol or a lower polyol or their mixtures, or an aqueous-alcoholic solution, may be employed as solubilising solvent. The monoalcohols or polyols which are particularly preferred are ethanol, isopropanol, propylene glycol or glycerine.

An embodiment of the invention is an emulsion in the form of protective cream or milk containing, in addition to the compounds of formula (I), fatty alcohols, ethoxylated fatty alcohols, esters of fatty acids and particularly triglycerides of fatty acids, fatty acids, lanolin, natural or synthetic oils, or waxes, in the presence of water.

Another embodiment consists of lotions such as oil-alcoholic lotions based on a lower alcohol such as ethanol, or a glycol such as propylene glycol and/or a polyol such as glycerine and esters of fatty acids such as the triglycerides of fatty acids.

The cosmetic composition of the invention may also be an aqueous-alcoholic gel incorporating one or more lower alcohols such as ethanol, propylene glycol or glycerine, and a thickener, in the presence of water.

The present invention is also aimed at cosmetic sunscreen compositions containing at least one compound of formula (I) which may be combined with other solar filters specific for UV-B radiation and/or UV-A radiation and compatible with the compounds according to the invention. It is consequently possible in this way to obtain a formulation which filters out both UV-B and UV-A radiations.

The present invention is also aimed at protective day creams containing at least one compound of formula (I) combined with at least one UV-A filter.

The compounds according to the invention may be combined with UV-B filters consisting of liposoluble compounds or of oils having filtering properties such as coffee oil in particular. Mention may be made, as lipophilic UV-B solar filters, of salicyclic acid derivatives such as 2-ethylhexyl salicylate, and homomenthyl salicylate, cinnamic acid derivatives, such as 2-ethylhexyl p-methoxycinnamate or 2-ethoxyethyl p-methoxycinnamate, p-aminobenzoic acid derivatives such as amyl p-aminobenzoate or 2-ethylhexyl p-dimethylaminobenzoate, benzophenone derivatives such as 2-hydroxy-2'-methoxybenzophenone or 2,2'-dihydroxy-4-methoxybenzophenone, camphor derivatives such as 3-(4'-methylbenzylidene)camphor, combined if appropriate with 4-isopropyldibenzoylmethane or 3-benzylidene camphor.

Mention can also be made, as hydrosoluble solar filters filtering out the UV-B rays, which may also be combined with the liposoluble or hydrosoluble filters of the invention provided that they are compatible with the latter, of the benzylidene camphor derivatives described in French Patent Nos. 2,199,971, 2,236,515 and 2,383,904 of the Applicant Company and more particularly 4-(2-oxo-3-bornylidenemethyl)phenyltrimethylammonium methylsulphate, and the salts of 4-(2-oxo-3-bornylidenemethyl)benzenesulphonic acid, 2-methyl-5-(2-oxo-3-bornylidenemethyl)benzenesulphonic acid and of 2-phenylbenzimidazole-5-sulphonic acid.

The compounds according to the invention may also be combined with UV-A filters, among which dibenzoylmethane derivatives may be mentioned.

It is to be understood that the list of solar filters employed in combination with the compounds (I) according to the invention which is shown above is not restrictive.

The sunscreen compositions according to the invention may be presented in the form of solutions, lotions, emulsions such as a cream or a milk, in the form of oils, fatty gels, aqueous-alcoholic or alcoholic gels, or may be packaged as an aerosol or as solid sticks. They may contain the abovementioned cosmetic adjuvants usually employed in compositions of this type.

The present invention is also aimed at coloured or uncoloured cosmetic compositions containing at least one compound of formula (I) as a protective agent against the UV-B rays.

These compositions may consist of hair care compositions such as hair lacquers, hair setting lotions optionally for treatment or disentangling, shampoos, colouring shampoos, hair dyeing compositions, of make-up products such as nail varnishes, skin treatment creams, foundations, lipsticks, as well as of any other cosmetic composition capable of presenting, on account of its components, problems of light stability during storage.

Another subject of the invention is a process for protecting human skin against UV rays, consisting in applying on the skin at least one compound of formula (I) present in a cosmetically acceptable medium and optionally combined with other agents absorbing the UV-A and/or UV-B rays.

The invention is also aimed at a process for protecting coloured cosmetic compositions against UV-B rays, consisting in incorporating at least one compound of formula (I) in these compositions.

We have also discovered in the course of our research that the 3-benzylidene camphor derivatives of formula (I) had interesting pharmacological activity in the field of topical and systemic treatment of acne, psoriasis and other dermatoses or inflammatory and allergic dermatological complaints, as well as anti-tumour activity.

Consequently, another subject of the invention is a pharmaceutical composition containing an effective quantity of at least one compound of formula (I) as active component, in a non-toxic carrier or excipient.

Such a composition may be employed in the topical and systemic treatment of benign or malignant neoplasias, of pre-malignant lesions, and in the systemic and topical prophylaxy of these ailments. It is suitable, in addition, for the treatment of dermatoses such as acne or psoriasis. It can also be employed orally with a view to treating certain rheumatic complaints such as, for example, chronic polyarthritis.

The compounds of formula (I) are usually administered orally in a daily dosage of approximately 2 $\mu$g to 5 mg per kg and preferably from 10 $\mu$g to 2 mg per kg.

The compositions for topical admininstration preferably contain from 0.0005% to approximately 5% by weight of compound of formula (I).

Any conventional non-toxic carriers or excipients may be employed as carrier or excipient for the pharmaceutical composition of the invention, the active compound being either in the form which is soluble, or in the form which is dispersed in the carrier.

The invention is illustrated by the following non-restrictive examples of application.

EXAMPLES OF FORMULATION

EXAMPLE 5

Protective day cream
Compound of Example 1: 1 g,
4'-Methoxy-4-tert.butyldibenzoylmethane sold under the name PARSOL 1789 by the company Givaudan: 0.5 g,
Sipol wax: 7 g,
Glycerol monostearate: 2 g,
Vaseline oil: 15 g,
Silicone oil: 1.5 g,
Cetyl alcohol: 1.5 g,
Glycerine: 10 g,
Preserving agent, perfume q.s
Water q.s.: 100 g.

EXAMPLE 6

Protective day cream
Compound of Example 3: 0.3 g,
4-Isopropyldibenzoylmethane sold under the name of EUSOLEX 8020 by the company MERCK: 0.6 g,
Benzylidene camphor: 0.5 g,
Triglycerides of $C_8$–$C_{12}$ fatty acids: 31 g,
Glycerol monostearate: 6 g,
Stearic acid: 2 g,
Cetyl alcohol: 1.2 g,
Lanolin: 4 g,
Propanediol: 2 g,
Triethanolamine: 0.5 g,
Preserving agent, perfume q.s.
Water q.s.: 100 g.

The creams of Examples 5 and 6 are prepared by heating the fatty substances to approximately 80°–85° C.; the filter(s) is (or are) then added.

The water and water-soluble components are heated separately to approximately 80°–85° C. and the oily phase is added to the aqueous phase with vigorous stirring. Stirring is continued for 10 to 15 minutes and the material is allowed to cool with moderate stirring.

EXAMPLE 7

Protective sunscreen milk
Sipol wax: 5 g,

Vaseline oil: 6 g,
Isopropyl myristate: 3 g,
Dimethylpolysiloxane: 1 g,
Cetyl alcohol: 1 g,
Glycerine: 20 g,
Compound of Example 2 (in sodium salt form): 2 g,
p-Methylbenzylidene camphor: 2 g,
Water q.s.: 100 g.

The compound of Example 2 is dissolved in water and glycerine. The p-methylbenzylidene camphor is dissolved in the fatty phase and this milk is prepared according to the usual techniques for producing an O/W emulsion.

EXAMPLE 8

Protective sunscreen cream
Compound of Example 4: 2 g,
4-[(2-Oxo-3-bornylidene)methyl]phenyltrimethylammonium methylsulphate: 2.5 g,
2-Hydroxy-4'-tert.butyldibenzoylmethane, prepared according to Example 1 of French Patent Application No. 2,506,156: 1 g,
Polyoxyethylenated fatty alcohols: 7 g,
Triglycerides of $C_8-C_{12}$ fatty acids: 30 g,
Glycerol monostearate: 2 g,
Silicone oil: 1.5 g,
Cetyl alcohol: 1.5 g,
Preserving agent, perfume q.s.
Water q.s.: 100 g.

The preparation of this cream is similar to that of Examples 5 and 6, the compound of Example 4 and 2-hydroxy-4'-tert.butyldibenzoylmethane being dissolved in the fatty phase, and 4-[(2-oxo-3-bornylidene)methyl]phenyltrimethylammonium methylsulphate being dissolved in the aqueous phase.

EXAMPLE 9

Oily sunscreen lotion
Compound of Example 1: 3 g,
Octyl p-dimethylaminobenzoate: 2 g,
Cocoa butter: 2.5 g,
Preserving agent, perfume q.s.
Triglycerides of $C_8-C_{12}$ fatty acids q.s.: 100 g.

The material is heated to approximately 40°–45° C. to homogenize the composition.

We claim:

1. A compound consisting of a derivative of 3-benzylidene camphor of the formula:

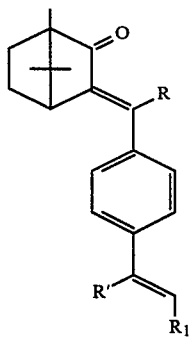

(I)

in which
R is a hydrogen atom, a methyl radical or an ethyl radical,
R' is a hydrogen atom, a methyl radical or an ethyl radical, with the proviso that if one of R and R' is a hydrogen atom, the other of R and R' is a methyl radical or an ethyl radical, $R_1$ is a $-COOR_2$, $-CONHR_2$, $-COO^-M^+$, $-CHO$, $-CH(OR_4)_2$ or $-CH_2OR_4$ group, $R_2$ is an alkyl, alkenyl, cycloalkyl or aralkyl radical containing at most 20 carbon atoms or said alkyl, alkenyl, cycloalkyl or aralkyl radical, substituted by hydroxy, alkoxy, amine or quaternary ammonium groups, M is a hydrogen atom, an alkali metal or a $N^+(R_3)_4$ group, $R_3$ being a hydrogen atom or a $C_1$ to $C_4$ alkyl or hydroxyalkyl radical, and $R_4$ is a hydrogen atom or an alkyl, cycloalkyl or aralkyl radical containing at most 20 carbon atoms.

2. Compound according to claim 1, in which if one of R and R' is a methyl radical the other of R and R' is an ethyl radical and if one of R and R' is an ethyl radical the other of R and R' is a methyl radical.

3. Compound according to claim 1, of formula:

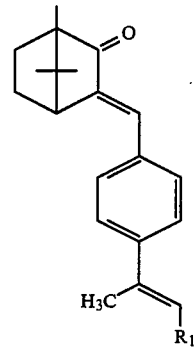

in which $R_1$ denotes the radical: $-COOC_2H_5$, $-COOH$ or $-CONHC_2H_5$.

4. Compound according to claim 1, of formula:

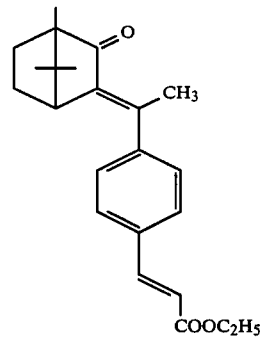

5. Process for preparing a compound of formula (I) according to claim 1, in which R is a hydrogen atom and R' is a methyl or ethyl radical, wherein
in a first stage a compound of formula:

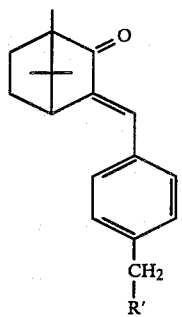

is subjected to bromination in an inert solvent medium, to obtain the compound of formula:

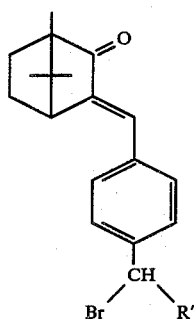

in a second stage the bromo derivative is hydrolysed with sodium hydroxide to obtain the secondary alcohol of formula:

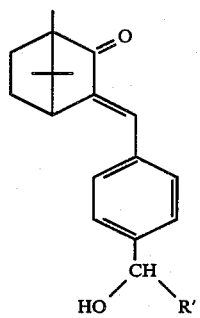

in a third stage the above secondary alcohol is oxidised to be converted to ketone of formula:

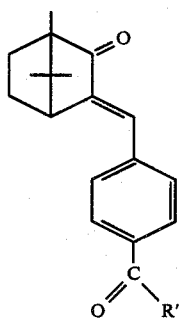

in a fourth stage, the above ketone is subjected to a Wittig-Horner condensation with a phosphonate of formula:

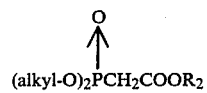

to obtain the compound of formula (I) in which R is a hydrogen atom, R' is methyl or ethyl and $R_1$ is —$COOR_2$.

6. Process for preparing a compound of formula (I) according to claim 1, in which R is a methyl or ethyl radical and R' is a hydrogen atom, wherein:

in a first stage a compound of formula:

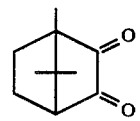

is subjected to a Wittig-Horner condensation with a phosphonate of formula:

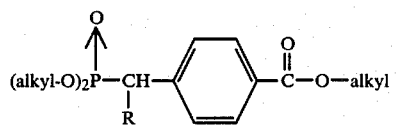

to obtain the compound of formula:

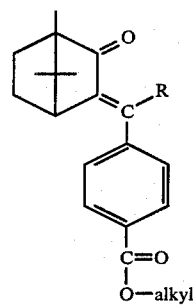

in a second stage, the alkoxycarbonyl group of the above compound is reduced in an inert solvent medium with the aid of a powerful reducing agent to obtain the primary alcohol of formula:

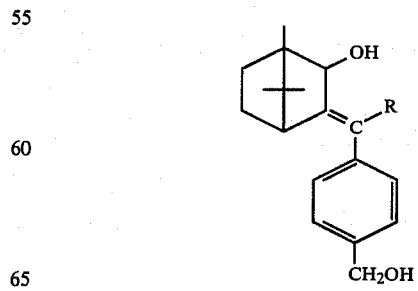

in a third stage, the above primary alcohol is oxidised to aldehyde of formula:

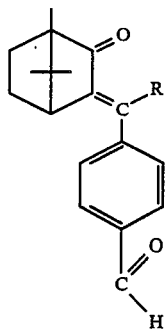

in a fourth stage, the above aldehyde is subjected to a Wittig-Horner condensation with a phosphonate of formula:

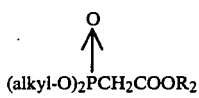

(alkyl-O)$_2$PCH$_2$COOR$_2$ to obtain the compound of formula (I) in which R is methyl or ethyl, R' is a hydrogen atom and R$_1$ is —COOR$_2$.

7. Process according to claim 5 or 6 for preparing compounds of formula (I) in which one of R and R' is a hydrogen atom and the other of R and R' is a methyl or ethyl radical and in which R$_1$ is a —COO$^-$M$^+$ group, M being a hydrogen atom, an alkali metal or a N$^+$(R$_3$)$_4$ group wherein R$_3$ is a hydrogen atom or a C$_1$ to C$_4$ alkyl or hydroxyalkyl radical wherein the compounds of formula (I) in which R$_1$ is —COOR$_2$, prepared according to claim 5 or 6, are saponified into corresponding acids in which R$_1$ is —COOH and the acids are converted into salts by an alkaline base or an amine to give the compounds of formula (I) in which R$_1$ is COO$^-$M$^+$, M$^+$ being as above defined.

8. Process according to claim 5 or 6 for preparing a compound of formula (I) in which one of R and R' is a hydrogen atom and the other of R and R' is a methyl or ethyl radical and in which R$_1$ is a —CHO or —CH(OR$_4$)$_2$ group, R$_4$ being a hydrogen atom or an alkyl, cycloalkyl or aralkyl radical containing at most 20 carbon atoms wherein the esters of formula (I) in which R$_1$ is —COOR$_2$, prepared according to claim 5 or 6, are reduced to be converted into alcohols of formula (I) in which R$_1$ is —CH$_2$OH, and then the alcohols are oxidized to obtain the corresponding aldehydes of formula (I) in which R$_1$ is —CHO, to which alkanols, cycloalkanols or aralkyl alcohols can be added in an acid medium to obtain the acetals of formula (I) in which R$_1$ is —CH(OR$_4$)$_2$.

9. Cosmetic composition which contains, as a protective agent against the UV-B rays, an effective amount of at least one derivative of 3-benzylidene camphor of formula (I) according to claim 1, in a cosmetically acceptable medium.

10. Cosmetic composition according to claim 9, which contains, as a protective agent against the UV-B rays, an effective amount of at least one compound of formula (I) as defined in claim 2, in a cosmetically acceptable medium.

11. Cosmetic composition according to claim 9 wherein the compound of formula (I) is present in proportions of between 0.5 and 15% by weight relative to the total weight of the composition.

12. Cosmetic composition according to claim 9 which contains at least one cosmetic adjuvant selected from the group consisting of thickeners, softeners, super-fatting agents, emollients, humectants, wetting agents, surfactants, preserving agents, anti-foams, perfumes, oils, waxes, colorants and pigments.

13. Cosmetic composition according to claim 9, in the form of sunscreen composition, which contains at least one compound of formula (I) combined with other hydrosoluble or liposoluble solar filters having a filtering effect in respect of the UV-B rays, selected from the group consisting of camphor derivatives, coffee oil, salicylic acid derivatives, cinnamic acid derivatives, p-aminobenzoic acid derivatives and benzophenone derivatives.

14. Cosmetic composition according to claim 9, in the form of protective day cream, which contains at least one compound of formula (I) combined with at least one UV-A filter.

15. Cosmetic composition according to claim 9, in the form of a coloured or uncoloured cosmetic composition, light-stabilized, which consists of a hair care composition selected from the group consisting of a hair lacquer, a hair setting lotion, a shampoo, a colouring shampoo, and a hair dyeing composition.

16. Process for protecting human skin against UV-B rays, wherein an effective amount of at least one compound of formula (I) defined in claim 1, contained in a cosmetically acceptable medium, is applied on the skin.

17. Process for protecting a coloured cosmetic composition against the UV-B rays, wherein an effective amount of at least one compound of formula (I) defined in claim 1, is incorporated in said composition.

18. Pharmaceutical composition which contains an effective amount of at least one compound of formula (I) according to claim 1 in a non-toxic carrier or excipient.

19. Process of claim 5, in which alkyl is methyl or ethyl.

20. Process of claim 6, in which alkyl is methyl or ethyl.

21. Process according to claim 5 or 6 for preparing compounds of formula (I) in which one of R and R' is a hydrogen atom and the other of R and R' is a methyl or ethyl radical and in which R$_1$ is a —CONHR$_2$ group, R$_2$ being an alkyl, alkenyl, cycloalkyl or aralkyl radical containing at most 20 carbon atoms or said alkyl, alkenyl, cycloalkyl or aralkyl radical substituted by hydroxy, alkoxy, amine or quaternary ammonium groups, wherein the compounds of formula (I) in which R$_1$ is —COOR$_2$, prepared according to claim 5 or 6, are saponified into corresponding acids in which R$_1$ is —COOH and the acids are converted into acid chlorides which are then reacted with an amine to form the corresponding amide of formula (I) in which R$_1$ denotes —CONHR$_2$.

22. Process according to claim 5 or 6 for preparing a compound of formula (I) in which one of R and R' is a hydrogen atom and the other of R and R' is a methyl or ethyl radical and in which R$_1$ is a —CH(OR$_4$)$_2$ group, R$_4$ being a hydrogen atom or an alkyl, cycloalkyl or aralkyl radical containing at most 20 carbon atoms, wherein the esters of formula (I) in which R$_1$ is —COOR$_2$, prepared according to claim 5 or 6, are reduced to be converted into alcohols of formula (I) in which R$_1$ is —CH$_2$OH, and then said alcohols are reacted directly with aldehydes in an acid medium to obtain the corresponding acetals of formula (I) in which $R_1$ denotes —$CH(OR_4)_2$.

23. Process according to claim 5 or 6 for preparing a compound of formula (I) in which one of R and R' is a hydrogen atom and the other of R and R' is a methyl or ethyl radical and in which $R_1$ is a —$CH_2OR_4$ group, $R_4$ being a hydrogen atom or an alkyl, cycloalkyl or aralkyl radical containing at most 20 carbon atoms, wherein the esters of formula (I) in which $R_1$ is —$COOR_2$, prepared according to claim 5 or 6, are reduced to be converted into alcohols of formula (I) in which $R_1$ is —$CH_2OH$, and then said alcohols are reacted with an alkyl, cycloalkyl or aralkyl halide to obtain the ethers of formula (I) in which $R_1$ denotes —$CH_2OR_4$.

24. Cosmetic composition according to claim 9, in the form of sunscreen composition, which contains at least one compound of formula (I) combined with solar filters filtering out the UV-A rays.

25. Cosmetic composition of claim 24, in which the solar filters are dibenzoylmethane derivatives.

26. Cosmetic composition of claim 14, in which the solar filters are dibenzoylmethane derivatives.

27. Cosmetic composition according to claim 9, in the form of a coloured or uncoloured cosmetic composition, light-stabilized, which consists of a make-up product selected from the group consisting of a nail varnish, a lipstick, a skin treatment cream and a foundation.

* * * * *